United States Patent [19]

Denney

[11] 4,454,230

[45] Jun. 12, 1984

[54] ASSAY METHOD AND REAGENT COMPOSITION FOR THE DETERMINATION OF MAGNESIUM

[75] Inventor: Jerry W. Denney, Indianapolis, Ind.

[73] Assignee: American Monitor Corporation, Indianapolis, Ind.

[21] Appl. No.: 397,002

[22] Filed: Jul. 12, 1982

[51] Int. Cl.$^3$ .................. G01N 33/20; G01N 33/52
[52] U.S. Cl. ...................................... 436/74; 422/61; 436/79; 436/175
[58] Field of Search ................... 436/74–79, 436/19, 175; 422/61

[56] References Cited

U.S. PATENT DOCUMENTS 3,754,864  8/1973  Gindler ............................ 436/74
4,383,043  5/1983  Denney et al. ..................... 436/74

OTHER PUBLICATIONS

Ingman; Microchemical Journal 10, 545–553 (1966).

Primary Examiner—Arnold Turk
Assistant Examiner—Michael S. Gzybowski
Attorney, Agent, or Firm—Marilyn L. Amick

[57] ABSTRACT

An improved assay method and reagent composition for the determination of magnesium in a fluid sample by reaction with an alkaline buffered solution of calmagite, in which caffeine and preferably also thiourea have been included, thereby achieving parity between protein-free and protein-containing samples while eliminating the need for cyanide.

7 Claims, No Drawings

ASSAY METHOD AND REAGENT COMPOSITION FOR THE DETERMINATION OF MAGNESIUM

BACKGROUND OF THE INVENTION

1. Field of the Invention

This invention relates to an improved method and reagent composition for determining magnesium levels in fluids, and more particularly to a colorimetric method which is performed directly on serum and other fluids without deproteinization.

2. Nature and Significance of Accurate Magnesium Determinations

Magnesium is extremely significant in human physiology. It is one of the most abundant cations in the body and, next to potassium, it is the most prevalent intracellular ion. Magnesium in its ionic form is essential to many physiological processes. It plays a vital and major role in carbohydrate and lipid metabolism by serving as an activator of adenosine triphosphate (ATP) in the transfer of energy rich phosphate. It is also essential as an activating ion for many enzymes involved in lipid, carbohydrate and protein metabolism. In muscle tissue, magnesium has a significant influence on neuromuscular apparatus. Magnesium ions are also essential for the preservation of the macromolecular structure of DNA, RNA and ribosomes, and in addition they play a vital part in bone formation and the maintenance of osmotic pressure.

The amount of magnesium in the body is particularly significant. Decreased levels of magnesium in the body produce muscle irritability which, if not corrected, can result in tetany (prolonged involuntary muscle spasms), which is clinically indistinguishable from that caused by decreased calcium levels, and convulsions. On the other hand, increased levels of magnesium have a curare-like effect, resulting in a loss of deep tendon reflexes, a loss of touch, temperature and pain sensation, respiratory failure, cardiac arrest.

Because of the vitally important roles magnesium plays in the normal functioning of life processes, it has long been recognized that it is necessary to be able to accurately and reliably measure magnesium levels in the body in order to aid the physician in diagnosis and treatment. In addition, it is correspondingly necessary that such results are able to be produced urgently in response to an emergency or STAT request from a physician. The ever-increasing recognition by clinicians of the need for frequent determinations of serum magnesium levels requires that the procedure desirably be capable of being performed by automated means. Of further importance, since blood samples obtained from pediatric or geriatric patients are usually very small, it is necessary that methods used for accurately determining magnesium levels desirably utilize no more than an extremely small sample volume.

3. Description of Prior Art

For many years, physicians regarded the determination of magnesium levels in serum or plasma to be of limited value due to the numerous errors to which the earlier techniques were subject, causing an unreliability which the prior art sought to avoid by several different approaches. In fact, even though improvements in certain respects were achieved, the great variety of methods still in current use for measuring the amount of magnesium in biological fluids is testament to the fact that none of them is completely satisfactory, even after long years of attempted improvement. Most are tedious, inaccurate or rely upon expensive instrumentation of limited usefulness which is not likely to be available except in the largest and most highly sophisticated clinical laboratories. Many difficulties have hindered the development of accurate and precise methods for the determination of magnesium, among which are the nonspecific nature of its precipitation reactions, the great liability to interference from other ions, and the relatively low intensity of its spectral lines.

Recently, direct colorimetric dye-complexing methods using indicators such as Magon, methylthymol blue, and calmagite have become increasingly popular. The direct dye-complexing methods which might be considered to be the most closely related of the prior art to the present method are those employing the dyestuff calmagite (3-hydroxy-4-[(2-hydroxy-5-methylphenyl)azo]-1-naphthalene-sulfonic acid). These methods involve the fact that calmagite is known to become "metallized" by reaction with several metal ions such as calcium, magnesium, iron, and copper to form a metallized complex which is colored and may be optically measured. The prior art has included EGTA (ethyleneglycol-bis[$\beta$-aminoethyl ether]-N,N'-tetra-acetic acid) and potassium cyanide to mask the metallizing of calmagite by metals other than magnesium, such as iron, copper, and calcium, which are normally found in blood serum and which might otherwise interfere in the assay. Thus magnesium is the primary metal in blood serum which metallizes or binds with calmagite in the prior art procedures. Unmetallized calmagite is blue in an alkaline medium, and when metallized or bound with magnesium, calmagite forms a reddish-colored complex. The blue, unmetallized calmagite compound, therefore, has a different spectral absorbance peak than does the metallized or magnesium bound compound.

The prior art method of Gindler (U.S. Pat. No. 3,754,864 issued Aug. 28, 1973) and Gindler et al. (Clin. Chem. 17, 1971, p. 662) incorporates those known properties of calmagite and its reaction with metal ions and also those known properties of EGTA and potassium cyanide to mask the metallizing of calmagite by iron, copper, and calcium normally found in blood; but the Gindler art also teaches that protein in serum produces a spectral shift in the absorbance of free and metallized calmagite, thus introducing errors when a non-protein, i.e. aqueous, solution is used for calibration. The unmetallized calmagite, which is blue in an alkaline medium (having an optimal absorbance between 600 and 650 nm) binds with magnesium to form a reddish-colored complex having an optimal absorbance of about 535 nm. The prior art teaches that the absorbance measurement at 532 nm is proportional to the amount of magnesium and thus serves as a quantitation of the amount of magnesium.

The Gindler prior art teaches that the spectral absorbance peak of the reddish-colored metallized dye is shifted in the presence of protein from 535 to 540 nm. In order to overcome this alleged interference from protein, selected micelle-forming protective colloids are added to the reaction mixture to mimic the interference from protein. These added substances, the prior art asserts, achieve spectral correlation between protein-containing and aqueous samples. Specifically, the prior art teaches that the absorbance peak of both protein-containing and aqueous samples is shifted to 545 nm when a micelle-forming protective colloid is added. Although this prior art method does achieve certain advantages over the earlier art, there remain or are created certain drawbacks, as now discussed.

The working reagent mixture of the Gindler et al. prior art is stable for no longer than several hours, thereby requiring not only the labor, cost and effort of reagent preparation every day, but the disposal and costly wastage of unused, prepared working reagent at the end of the day, and inaccuracy or unworkability if attempted to be used after that short stability period.

The addition of a micelle-forming protective colloid is believed, according to the novel concepts of the present invention, to unnecessarily complicate the formulation and possibly introduces adverse properties to the assay. The prior art teaches a measurement at 532 nm (even though it teaches a spectral shift to 545 nm), which is close to the absorbance of chromogenic substances such as hemoglobin, bilirubin, and lipemia which may be present in certain patients' serum. Consequently, when measurements are made at 532 nm on serum which contains hemoglobin, bilirubin or which is lipemic, the absorbance of these substances is likely to be wrongly determined as being due to the presence of magnesium. Therefore, the analyst could be led to report a higher level of magnesium to be present in the patient's blood serum than is actually present, thereby potentially leading the physician to a mistaken diagnosis or improper treatment of the patient, with obviously dangerous or other disadvantageous results.

Furthermore, the normal range of serum magnesium levels is a very narrow one, i.e., ranging from only 1.7 to 2.1 milliequivalents per liter of serum, and it is readily apparent that a clinically useful assay for magnesium must provide sufficient accuracy and sensitivity to accurately distinguish between normal and pathological levels. The limited sensitivity of the prior art methods for magnesium measurement diminish the likelihood of precise measurements of serum magnesium levels.

More recently, Denney et al. in co-pending U.S. patent application (Ser. No. 282,721, filed July 13, 1981), now U.S. Pat. No. 4,383,043, issued on May 10, 1983, the content of which is hereby incorporated by reference, describe an improved colorimetric assay method and reagent which help to solve or minimize many of the problems which plagued the prior art methods described above. The present invention provides even further improvement and/or an alternative means for improving upon these prior art methods.

SUMMARY OF THE INVENTION

Accordingly, it is therefore a general object of the present invention to provide a novel reagent composition and method for the colorimetric, quantitative determination of magnesium in fluids. A more particular object of the present invention is to provide a method which uses a metal complexing agent, which can be accurately performed directly on fluid samples containing protein, and which may be calibrated using materials which are protein-free. A further object is to provide a magnesium method which is rapid and suitable for use with a variety of generally available automated laboratory instrumentation. Another object is to provide a reagent composition with extended stability and which does not require the use of cyanide. These and other objects, features, and advantages will be apparent from the following description of the presently preferred embodiments of the present invention.

It was discovered that when caffeine and thiourea are included in a buffered alkaline solution containing calmagite and EGTA, the objects and goals of the present invention are achieved. The buffered alkaline solution is preferably of the nature as described and set forth in the previously mentioned Denney et al. related application. That is, the solution should be alkalinized to a pH of approximately 11 using a buffer whose $pK_a$ is greater than 8, thereby yielding a buffered solution whose relative Van Slyke buffer value is between approximately 3 and 15. The amount of calmagite in the solution is easily determined by one knowledgeable in the art, and is dependent to an extent upon the specific requirements of the assay conditions and purity of the raw material. As in prior art methods, EGTA is included in the reagent to preferentially bind calcium ions which would otherwise react with the calmagite and mistakenly be measured as magnesium, thereby yielding falsely elevated results. Further, the buffered solution preferably also contains dimethylsulfoxide for its stabilizing effects on the reagent.

Caffeine is added to the solution in a preferred concentration of at least approximately 0.2% by weight. However, amounts from 0.1% to 5% or greater may be used effectively. When caffeine is included in the reagent, it has been discovered that, when calibrating the assay with aqueous (protein-free) material, results obtained on untreated human patient serum specimens are substantially equivalent to those obtained when calibrating the assay with protein-based material. This is especially surprising since the Gindler prior art expressly teaches that a micelle-forming protective colloid must be present to correct for spectral differences between aqueous and protein-containing samples.

It appears that the ability of calmagite to bind with magnesium ions is significantly enhanced or accelerated with respect to any spectral shifting, and it is postulated that the caffeine promotes or facilitates the release of magnesium from the protein molecule. This then presumably makes more of the protein-bound magnesium exposed and available for binding with the dye, thereby accelerating or otherwise promoting the reaction, and thereby also increasing the accuracy of the assay.

To prevent interference from heavy metal ions, i.e. iron, copper, zinc, cobalt, nickel, and lead, thiourea has been discovered to be quite effective, and when included in the reagent along with caffeine, thiourea has been found to be as effective for this purpose as the highly toxic and poisonous cyanide, which has heretofore been used by the prior art.

One or more surfactants, which are already known to be beneficial in minimizing adverse effects from turbidity or endogenous lipoproteins that may occasionally be encountered in patient serum or commercial quality control products, may optionally also be added. However, when caffeine is included in the solution, the need to also include such surfactants has been shown to be obviated, except perhaps as a possible safeguard against an occasional, severely turbid sample.

Optionally also, the reagent may have included therein a quantity of a salt to maintain proper ionic strength of the reaction mixture, which is especially desirable and recommended when the assay is to be performed on blood serum samples.

To use the reagent composition of the present invention to perform an assay for magnesium, a sample of serum or other fluid is combined with the reagent. The formation of the red calmagite-magnesium complex is a measure of the amount of magnesium in the sample and may be optically measured, either by photometric measurement at about 547 nm of the reddish-colored complex itself, or by photometric measurement at about 610 nm of the amount of the blue, unbound calmagite remaining in the reaction mixture.

Calibration of the assay may be made with equal accuracy using either materials which are aqueous and protein-free or materials which contain protein, thereby making the assay especially versatile and useful for virtually any situation wherein an assay for magnesium is desired.

Although the present invention can be practiced by additions of the desired ingredients to the sample individually or in the form of one or more reagent combinations, it is customary and convenient for laboratory and other analytical personnel to use pre-formulated compositions, or reagents, which are generally known as "kits", and which are available on a commercial basis from various manufacturers. A kit may contain one or more preformulated reagents and appropriate calibration and quality control materials, or the kit may be in the form of one or more pre-formulated reagents packaged individually or in bulk form for a specific intended use.

With respect to the present invention, it is desirable that the kit contain two separate pre-formulated reagents, one containing the calmagite and the other containing the alkaline buffering agent. Either or both reagents may also contain additional desired ingredients such as surfactants, antimicrobial agents, and so forth. With respect to the present invention, the caffeine may be added to either reagent, but solubility has been found to be better if included in the alkaline buffer.

DESCRIPTION OF THE PREFERRED EMBODIMENTS

The specific embodiments of the present invention detailed herein are provided to enable an analyst skilled in the art to understand and make reagent compositions and to perform an assay according to the novel concepts and achievements of the present invention.

EXAMPLE 1

Reagent Preparation

A buffer reagent is prepared by combining the following substances in the amount indicated in approximately 800 milliliters of deionized water:
2-amino-2-methyl-1-propanol: 93.6 grams
caffeine: 4.0 grams
thiourea: 0.5 grams
potassium chloride: 50.7 grams Adjust to pH 11.6 using hydrochloric acid, then bring volume to 1.0 liter using deionized water.

A dye reagent is prepared by combining the following substances in the amount indicated in approximately 800 milliliters of deionized water:
calmagite: 0.072 grams
EGTA: 0.083 grams
dimethylsulfoxide: 100 milliliters Adjust pH to 6.0 using hydrochloric acid, then bring volume to 1.0 liter using deionized water.

A diagnostic reagent for the determination of magnesium is then prepared by combining equal quantities of the buffer reagent and the dye reagent. The reagent thus prepared has a pH of about 11.3 and will retain its usefulness for several months or longer.

EXAMPLE 2

Determination of Magnesium

To perform an assay for magnesium, 5.0 milliliters of the reagent and 50 microliters of the sample to be assayed are mixed together. After one minute, the absorbance (A) of the reaction mixture is measured at 547 nm. For calibration, a sample containing a known amount of magnesium is similarly treated.

To calculate the amount of magnesium in the sample, divide the $A_{547}$ of the unknown by the $A_{547}$ of the calibrator, then multiply the result thus obtained by the known amount of magnesium in the calibrator.

EXAMPLE 3

Determination of Magnesium

Using an automated chemical analyzer capable of performing mathematical comparisons involving a color loss, an amount of the sample to be assayed and an amount of the reagent are combined in the preferred ratio of 1 part sample to 100 parts of the reagent. The amount of resultant loss in color at 620 nm is then measured and compared to the loss observed with a calibrator of known magnesium concentration. The KDA (Reg. TM, American Monitor Corporation) analyzer has been used in carrying out this embodiment of the present invention.

Although a final caffeine concentration of 0.2% by weight is presented in the preferred embodiment set forth herein, amounts up to 5% or greater may be used in the practice of the present invention. The beneficial effects derived from additional amounts of caffeine, however, do not increase proportionately, and 0.2% has been found to be an adequate concentration to meet the requirements of most clinical situations.

Minor variations from the quantity of thiourea presented may similarly be made without departing from the inventive concepts; however, a final concentration not in excess of 3% should be sufficient to adequately prevent interference from any level of heavy metal that might be encountered in a clinical situation.

Optical measurements using reflectance techniques rather than absorbance or transmittance techniques may also be employed. Other modifications and perturbations to the foregoing embodiments will be apparent to those skilled in the art and are not to be considered beyond the scope of the novel concepts of the present invention.

What is claimed is:

1. In a reagent composition for the determination of magnesium in a protein-containing fluid by rection with alkaline calmagite, the improvement wherein said composition comprises at least about 0.1% by weight caffeine, thereby reducing protein interference.

2. A composition as recited in claim 1, further comprising thiourea.

3. A method for the determination of magnesium in a protein-containing fluid, comprising the steps of:
   (a) combining a sample of said fluid with a reagent to form a reaction mixture, said reagent comprising:
      (i) an alkaline buffer,
      (ii) calmagite,
      (iii) an agent to complex heavy metals, and
      (iv) at least about 0.1% by weight caffeine; and
   (b) measuring the absorbance of said reaction mixture.

4. A method as recited in claim 3, wherein the agent to complex heavy metals is thiourea.

5. A diagnostic kit for the determination of magnesium in a protein-containing fluid, said kit having included therein the ingredients:
 (a) an alkaline buffer,
 (b) calmagite,
 (c) an agent to complex heavy metals, and
 (d) at least about 0.1% by weight caffeine;
said ingredients being included in the form of at least one pre-formulated reagent.

6. A kit as recited in claim 5, wherein the agent to complex heavy metals is thiourea.

7. A diagnostic kit for the determination of magnesium in a protein-containing fluid, said kit comprising:
 (a) a first reagent comprising about 9.4% by weight 2-amino-2-methyl-1-propanol, about 0.4% by weight caffeine, about 0.05% by weight thiourea, and about 5% by weight potassium chloride; and
 (b) a second reagent comprising about 0.01% by weight calmagite, about 0.01% by weight EGTA and about 10% by weight dimethylsulfoxide.

* * * * *